(12) United States Patent
Olek et al.

(10) Patent No.: US 11,753,683 B2
(45) Date of Patent: Sep. 12, 2023

(54) MCC AS EPIGENETIC MARKER FOR THE IDENTIFICATION OF IMMUNE CELLS, IN PARTICULAR BASOPHIL GRANULOCYTES

(71) Applicant: Precision for Medicine GmbH, Berlin (DE)

(72) Inventors: Sven Olek, Berlin (DE); Udo Baron, Berlin (DE)

(73) Assignee: Precision for Medicine GmbH, Berlin (DE)

( * ) Notice: Subject to any disclaimer, the term of this patent is extended or adjusted under 35 U.S.C. 154(b) by 178 days.

(21) Appl. No.: 16/758,082

(22) PCT Filed: Oct. 24, 2018

(86) PCT No.: PCT/EP2018/079168
§ 371 (c)(1),
(2) Date: Apr. 22, 2020

(87) PCT Pub. No.: WO2019/081584
PCT Pub. Date: May 2, 2019

(65) Prior Publication Data
US 2021/0189489 A1 Jun. 24, 2021

(30) Foreign Application Priority Data
Oct. 25, 2017 (DE) .......................... 102017125013.1

(51) Int. Cl.
*C12Q 1/6881* (2018.01)
(52) U.S. Cl.
CPC ..... *C12Q 1/6881* (2013.01); *C12Q 2600/154* (2013.01)
(58) Field of Classification Search
None
See application file for complete search history.

(56) References Cited

U.S. PATENT DOCUMENTS

| 2007/0243531 | A1 | 10/2007 | Kohonen-Corish | |
| 2016/0024578 | A1* | 1/2016 | Olek | C12Q 1/686 506/2 |

FOREIGN PATENT DOCUMENTS

| WO | WO 2005/071404 A1 | 8/2005 | |
| WO | WO 2012/162660 A2 | 11/2012 | |
| WO | WO 2013/033627 A2 | 3/2013 | |
| WO | WO 2014/170497 A2 | 10/2014 | |
| WO | WO-2014170497 A2 * | 10/2014 | ........... C12Q 1/6851 |

OTHER PUBLICATIONS

Feng, Suhua et al. Conservation and divergence of methylation patterning in plants and animals. PNAS 2010 vol. 107 No. 19 pp. 8689-8694).*
GenBank Accession AC126917 (Aug. 16, 2002).*
Accomando et al., Quantitative reconstruction of leukocyte subsets using DNA methylation, Genome Biol. Mar. 5, 2014, 15(3).
Antequera and Bird, Number of CpG Islands and Genes in Human and Mouse, Proc Natl Academy of Science USA 90: 11995-9, 1993.
Booth, Michael J. et al., Quantitative Sequencing of 5-Methylcytosine and 5-Hydroxymethylcytosine at Single-Base Resolution, Science May 18, 2012, vol. 336, No. 6083, pp. 934-937.
Esteller, M., CpG Island Hypermethylation and tumor Suppressor Genes: a Booming Present, a Brighter Future, Oncogene 21:5427-5440, 2002.
Jones and Laird, Cancer-Epigenetics Comes of Age, Nature Genetics 21: 163-167, 1999.
Kohonen-Corish et al., Promoter methylation of the mutated in colorectal cancer gene is a frequent early event in colorectal cancer, Ocogene, Jun. 28, 2007; 26(30): 4435-4441.
Kristensen and Hansen, PCR-Based Methods for Detecting Single-Locus DNA Methylation Biomarkers in Cancer Diagnostics, Prognostics, and Response to Treatment, Clinical Chemistry 55:8 1471-1483 (2009).
Laird, Peter W., The Power and The Promise of DNA Methylation Markers, Nature Reviews Cancer 3, pp. 253-266 (2003).
Mozhui, K. et al., Ancestry dependent DNA methylation and influence of maternal nutrition, PLoS One (2015) 10(3) e0118466, pp. 1-17.

* cited by examiner

*Primary Examiner* — Amanda Haney
(74) *Attorney, Agent, or Firm* — BakerHostetler

(57) ABSTRACT

The present invention relates to a method, in particular an in vitro method, for identifying basophil granulocytes, comprising analyzing a modification such as for example the methylation status of at least one CpG position in the mammalian gene region for the gene "mutated in colorectal cancer" (MCC), wherein a demethylation or lack of modification or methylation of said gene region is indicative for a basophil granulocyte, when compared to a non-basophil granulocyte, or any other cell type in the peripheral blood or in other tissues. The analyses according to the invention can identify basophil granulocytes on an epigenetic level and distinguish them from all other cells in complex samples, such as, for example, other blood or immune cells. The present invention furthermore provides an improved method for quantifying basophil granulocytes, in particular in complex samples. The method can be performed with or without a step of purifying and/or enriching cells, preferably in whole blood and/or non-trypsinized tissue. Finally, the invention provides primers, probes and amplicons based on bisulfite treated nucleic acids.

15 Claims, 1 Drawing Sheet
Specification includes a Sequence Listing.

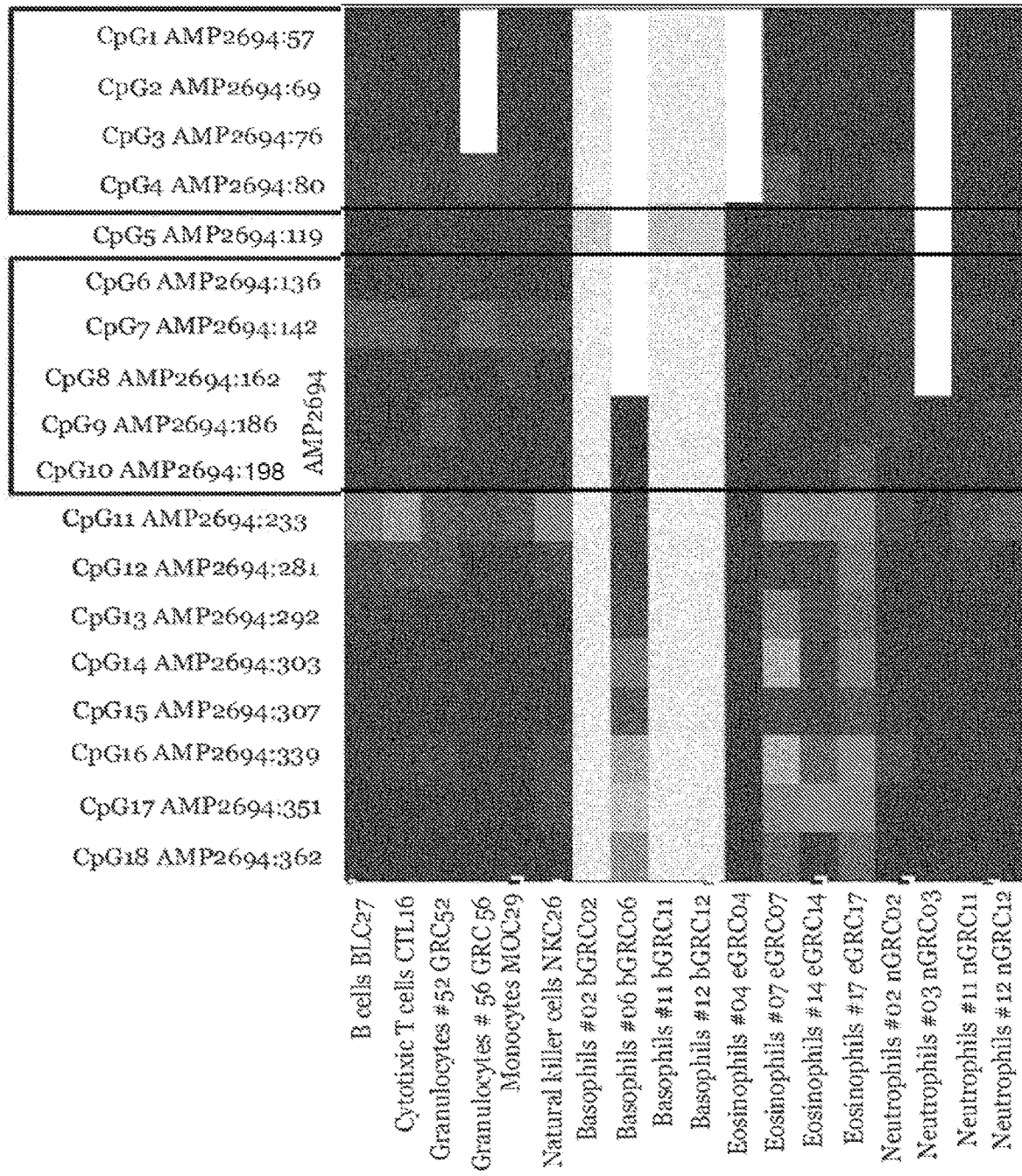

MCC AS EPIGENETIC MARKER FOR THE IDENTIFICATION OF IMMUNE CELLS, IN PARTICULAR BASOPHIL GRANULOCYTES

CROSS-REFERENCE TO RELATED APPLICATIONS

This application is a 35 U.S.C. § 371 national phase application of International Patent Application No. PCT/EP2018/079168, filed Oct. 24, 2018, which claims priority to German Patent Application No. 102017125013.1, filed Oct. 25, 2017, all of which are incorporated herein by reference in their entirety.

SEQUENCE LISTING

The Sequence Listing for this application is labeled "113828.000023_Sequence Listing.txt", which was created on Apr. 20, 2020 and is 4 Kilobytes. The entire content is incorporated herein by reference in its entirety.

The present invention relates to a method, in particular an in vitro method, for identifying basophil granulocytes, comprising analyzing a modification such as for example the methylation status of at least one CpG position in the mammalian gene region for the gene "mutated in colorectal cancer" (MCC), wherein a demethylation or lack of modification or methylation of said gene region is indicative for a basophil granulocyte, when compared to a non-basophil granulocyte, or any other cell type in the peripheral blood or in other tissues. The analyses according to the invention can identify basophil granulocytes on an epigenetic level and distinguish them from all other cells in complex samples, such as, for example, other blood or immune cells. The present invention furthermore provides an improved method for quantifying basophil granulocytes, in particular in complex samples. The method can be performed with or without a step of purifying and/or enriching cells, preferably in whole blood and/or non-trypsinized tissue.

Furthermore, the present invention relates to a kit for performing the above methods as well as respective uses thereof. It is one aim of this invention to provide a novel, more robust means to quantitatively detect and measure basophil granulocytes of the blood within any solid organs or tissue or any body fluid of a mammal. BACKGROUND OF THE INVENTION Granulocytes account for about 60% of all white blood cells, also referred to as leukocytes. Their main function is phagocytosis, i.e. the digestion of foreign cells like bacteria, viruses and other parasites. Granulocytes can be distinguished from other leukocytes, such as monocytes and lymphocytes, by the presence of intracellular granules filled with enzymes that help digest foreign cells. Granulocytes are also referred to as polymorphonuclear leukocytes (PMN, PML, or PMNL) because of the varying shapes of their nucleus, which is usually lobed into three segments. Three forms of granulocytes exist, the so-called neutrophil, eosinophil and basophil granulocytes. Their names are derived from their ability to be stained by different dyes; for example granules in neutrophils can be stained by neutral dyes, while granules in basophils can be stained by basic dyes.

Basophil granulocytes are the least numerous of the granulocytes and account for about 0.01% to 0.3% of all circulating leukocytes. They participate in the hypersensitivity of inflammatory reactions, which causes allergic symptoms. When stimulated, basophil granulocytes release histamine, which helps trigger inflammation, as well as heparin, which prevents blood from clotting. The presence of protein receptors on the cell surface of basophil granulocytes enables the binding of IgE, which facilitates a selective response to environmental substances, such as pollen proteins.

Even though almost all cells in an individual contain the exact same complement of DNA code, higher organisms must impose and maintain different patterns of gene expression in the various types of tissue. Most gene regulation is transitory, depending on the current state of the cell and changes in external stimuli. Persistent regulation, on the other hand, is a primary role of epigenetics—heritable regulatory patterns that do not alter the basic genetic coding of the DNA. DNA methylation is the archetypical form of epigenetic regulation; it serves as the stable memory for cells and performs a crucial role in maintaining the long-term identity of various cell types. Recently, other forms of epigenetic regulation were discovered. In addition to the "fifth base" 5-methylcytosine (mC), a sixth (5-hydroxymethylcytosine, hmC), seventh (5-formylcytosine, fC) and eighth (5-carboxycytosine, cC) can be found (Michael J. Booth et al. Quantitative Sequencing of 5-Methylcytosine and 5-Hydroxymethylcytosine at Single-Base Resolution Science 18 May 2012, Vol. 336 no. 6083 pp. 934-937).

The primary target of mentioned DNA modifications is the two-nucleotide sequence Cytosine-Guanine (a 'CpG site'); within this context cytosine (C) can undergo a simple chemical modification to become formylated, methylated, hydroxymethylated, or carboxylated. In the human genome, the CG sequence is much rarer than expected, except in certain relatively dense clusters called 'CpG islands'. CpG islands are frequently associated with gene promoters, and it has been estimated that more than half of the human genes have CpG islands (Antequera and Bird, Proc Natl Acad Sci USA 90: 11995-9, 1993).

Aberrant methylation of DNA is frequently associated with the transformation from healthy to cancerous cells. Among the observed effects are genome-wide hypomethylation, increased methylation of tumor suppressor genes, and hypomethylation of many oncogenes (reviewed, for example, by Jones and Laird, Nature Genetics 21:163-167, 1999; Esteller, Oncogene 21:5427-5440, 2002; and Laird, Nature Reviews/Cancer 3:253-266, 2003). Methylation profiles have been recognized to be tumor specific (i.e., changes in the methylation pattern of particular genes or even individual CpGs are diagnostic of particular tumor types), and there is now an extensive collection of diagnostic markers for bladder, breast, colon, esophagus, stomach, liver, lung, and prostate cancers (summarized, for example, by Laird, Nature Reviews/Cancer 3:253-266, 2003).

For one of the recently described modification of cytosine, 5-hydroxymethylation, the utility of oxidative bisulfite sequencing to map and quantify 5 hmC at CpG islands was shown (Michael J. Booth et al. Quantitative Sequencing of 5-Methylcytosine and 5-Hydroxymethylcytosine at Single-Base Resolution Science 18 May 2012, Vol. 336 no. 6083 pp. 934-937). High levels of 5hmC were found in CpG islands associated with transcriptional regulators and in long interspersed nuclear elements. It is suggested that these regions might undergo epigenetic reprogramming in embryonic stem cells.

WO 2012/162660 describes methods using DNA methylation arrays are provided for identifying a cell or mixture of cells and for quantification of alterations in distribution of cells in blood or in tissues, and for diagnosing, prognosing and treating disease conditions, particularly cancer. The methods use fresh and archival samples.

US 2007/0243531 discloses a method of diagnosing colorectal cancer by determining the degree of methylation of a nucleic acid that regulates the expression of the MCC gene. Methylation of the MCC gene itself is not mentioned.

Kohonen-Corish et al. (in: Kohonen-Corish et al. Promoter methylation of the mutated in colorectal cancer gene is a frequent early event in colorectal cancer) disclose MCC gene hypermethylation at promoter CpG islands to be a frequent and early change during colorectal carcinogenesis. Promoter methylation causes gene silencing of the colorectal tumor suppressor gene MCC, promoting the progression of the disease. No evidence for methylation of CpG positions outside of the MCC promoter is described.

Accomando et al. (in: Accomando et al. Quantitative reconstruction of leukocyte subsets using DNA methylation. Genome Biol. 2014 Mar. 5; 15(3)) disclose that cell lineage-specific DNA methylation patterns distinguish normal human leukocyte subsets and can be used to detect and quantify these subsets in peripheral blood. They used DNA methylation to simultaneously quantify multiple leukocyte subsets and to identify cell lineage-specific DNA methylation signatures that distinguish human T cells, B cells, NK cells, monocytes, eosinophils, basophils and neutrophils. MCC is not mentioned.

Mozhui, K. et al. (Ancestry dependent DNA methylation and influence of maternal nutrition. PLoS One (2015) 10(3): e0118466, pages 1-17) describe stable inherited (imprinted) methylation pattern in the gene for MCC.

WO 2005/071404 discloses methylation of MCC as a marker for colon cancer.

In view of the above, it is an object of the present invention to provide an improved and in particular robust method based on DNA-methylation analysis as a superior tool in order to more conveniently and reliably detect, identify, discriminate, and quantify basophil granulocytes.

The present invention solves the above object by providing a method for identifying basophil granulocytes in a sample, comprising analyzing a modification, such as, for example, the methylation status of at least one CpG position in the mammalian gene region for mutated in colorectal cancer (MCC), wherein preferably said gene region as analyzed is positioned according to SEQ ID NO: 1, wherein a demethylation or lack of modification, such as, for example, methylation of said gene region is indicative for a basophil granulocyte, when compared to a non-basophil granulocyte. A "modification" includes epigenetic regulation in addition to the "fifth base" 5-methylcytosine (mC), i.e. 5-hydroxymethylcytosine (hmC), 5-formylcytosine (fC), and 5-carboxycytosine (cC).

The human mutated in colorectal cancer (MCC) gene is a candidate colorectal tumor suppressor gene. The MCC protein is known to negatively regulate cell cycle progression and to suppress the Wnt/beta-catenin pathway. Downstream targets of MCC include phospho-ERK, c-Myc, p27, cyclin B1, Mcl-1, caspases 8 and 3. MCC is further involved in cell migration independently of RAC1, CDC42 and p21-activated kinase activation. The gene for human MCC is found on chromosome 5, 113,022,099-113,488,830 reverse strand, Ensembl-ID: ENSG00000171444.

Granulocytes (GRCs) are a group of cell comprising basophiles (bGRCs), neutrophils (nGRCs), and eosinophils (eGRCs).

In the context of the present invention, a "gene" or "gene region" shall comprise all of the genomic region relating to (e.g. regulating) and encoding for MCC. Thus, included are enhancer regions, promoter region(s), introns, exons, and non-coding regions (5'- and/or 3'-regions) that belong to MCC. Preferred is thus a method according to the present invention, wherein the at least one CpG position is present in the 5' region upstream from the transcription start, promoter region, the 5' or 3' untranslated regions, exon, intron, exon/intron border and/or in the 3' region downstream of the transcriptional stop of the gene as analyzed.

The present invention is further based on the surprising identification of a region of the MCC gene by the inventors, as specific epigenetic marker, allowing the identification of basophil granulocytes as well as the clinical routine application of said analysis.

In the context of the present invention, the genomic region of MCC, in particular according to SEQ ID NO: 1 allows the identification of basophil granulocytes. Surprisingly, the discriminatory pattern of bisulfite convertible and non-convertible cytosine is particularly and even exclusively limited to the genomic region according to SEQ ID NO: 1 for basophil granulocytes as shown using the amplicon according to SEQ ID NO: 1, and in particular in the bisulfite converted sequences according to SEQ ID NO: 2 and/or 3.

The inventors could demonstrate that in the basophil granulocytes the CpG motifs as disclosed are almost completely demethylated (i.e. to more than 70%, preferably 80%, preferably more than 90% and most preferred more than 95%), whereas the same motifs are completely methylated in all other immune cells.

The differential methylation of the CpG motifs within the aforementioned regions is a valuable tool to identify basophil granulocytes, such as will be required/or at least of some value for identifying and quantifying said cells in autoimmune diseases, transplant rejections, cancer, allergy, primary and secondary immunodeficiencies, such as, for example, HIV infections and AIDS, Graft versus Host (GvH), hematologic malignancies, rheumatoid arthritis, multiple sclerosis, or a cytotoxic T cell related immune status in any envisionable diagnostic context. The assay allows measurement of basophil granulocytes without purification or any staining procedures.

Another preferred aspect of the method according to the present invention then further comprises a quantification of the relative amount of basophil granulocytes based on comparing relative amounts of said methylation frequency in the region as analyzed with relative amounts of the methylation frequency in a control gene, such as, for example, GAPDH. Said quantification is thus achieved based on the ratio of the bisulfite convertible DNA to nonconvertible DNA in the genetic region of MCC (e.g. of SEQ ID NO: 1) as described and analyzed herein. Most preferred is a quantification of the relative amount of basophil granulocytes is based on an (preferably parallel or simultaneous) analysis of the relative amount of bisulfite convertible DNA of cell-specific region for MCC, and of the relative amount of bisulfite convertible DNA of cell-unspecific genes (preferably designated "control genes" or "control regions", such as, for example, the gene for GAPDH).

In a further preferred embodiment of the method according to the present invention, said analysis of bisulfite convertibility comprises amplification with at least one primer of suitable primer pairs that can be suitably designed based on SEQ ID NO: 1, preferably oligomers according to any of SEQ ID NO: 4 to 11.

In contrast to FACS and mRNA measurements, using the methods according to the present invention, the measurement(s) and analyses can be done independent of purification, storage—and to quite some extent—also to tissue quality.

Preferably, the amplification involves a polymerase enzyme, a PCR or chemical amplification reaction, or other amplification methods as known to the person of skill as described below, e.g. in the context of MSP, HeavyMethyl, Scorpion, MS-SNUPE, MethylLight, bisulfite sequencing, methyl specific restriction assays and/or digital PCR (see, for example Kristensen and Hansen PCR-Based Methods for Detecting Single-Locus DNA Methylation Biomarkers in Cancer Diagnostics, Prognostics, and Response to Treatment Clinical Chemistry 55:8 1471-1483 (2009)).

With the amplification, an amplicon of the MCC gene region is produced that is a particularly preferred "tool" for performing the method(s) according to the present invention. Consequently, oligomers according to any of SEQ ID NO: 4 and 5 or an amplicon as amplified by a primer pair based on SEQ ID NO: 4 and 5 or 6 and 7 or 9 and 10 as mentioned herein constitute preferred embodiments of the present invention. Thus, the sequences of SEQ ID NO: 1 to 3 (and, if needed, the complementary sequences thereto) can be used to design primers for amplifications, i.e. serve as "beacons" in the sequence as relevant. Similarly, additional primers and probes can be designed based on the amplicon according to SEQ ID NO: 1. Amplification can take place either in the genomic and/or bisulfite (i.e. "converted") DNA sequence.

The person of skill will furthermore be able to select specific subsets of CpG positions in order to minimize the amount of sites to be analyzed, for example at least one of CpG position selected from a CpG position in an amplicon according to SEQ ID NO: 1, and is preferably selected from CpG positions 57, 69, 76, 80, 119, 136, 142, 162, 186, 198, 233, 281, 292, 303, 307, 339, 351, and 362 in the amplicon No. 2694 according to SEQ ID NO: 1. The positions are numerically counted from the 5'-end of an amplicon as generated and analyzed, and are designated in FIG. 1. Preferred are combinations of all, 9, 4 or 5 positions (see boxes), the analysis of which produces sufficient data and/or information in order to be informative in the context of the present invention.

The person of skill will furthermore be able to select specific subsets of CpG positions in order to minimize the amount of sites to be analyzed, for example at least one of CpG position 186 and/or 198 in the amplicon No. 2694 of the MCC specific bisulfite convertible region (SEQ ID NO: 1), or all sites as present on the bisulfite convertible region according to SEQ ID NO: 1.

In order to analyze the bisulfite convertibility of CpG positions, any known method to analyze DNA methylation can be used. In a preferred embodiment of the method according to the present invention, the analysis of the methylation status comprises a method selected from methylation specific enzymatic digests, bisulphite sequencing, analysis selected from promoter methylation, CpG island methylation, MSP, HeavyMethyl, MethylLight, Ms-SNuPE or other methods relying on a detection of amplified DNA. These methods are well known to the person of skill, and can be found in the respective literature.

In a preferred embodiment of the method according to the present invention, said method is suitable for routine application, for example on a DNA-chip. Based on the above information and the respective literature, the person of skill will be able to adjust the method as above to such settings.

In yet another preferred embodiment of the methods according to the present invention, said method is performed without a step of purifying and/or enriching said cells to be identified, preferably using whole blood and/or non-trypsinized tissue.

In another preferred embodiment of the method according to the present invention, the identification comprises a distinction of said basophil granulocytes from all major peripheral blood cell types and/or non-blood cells, preferably, but not limited to, from follicular helper T cells, cytotoxic T-cells, granulocytes, basophil granulocytes, NK-cells, and T-helper cells, and other cell types derived from other organs than blood.

In yet another preferred embodiment of the method according to the present invention, the sample is selected from a mammalian body fluid, including human blood samples, or a tissue, organ or a sample of leukocytes or a purified or separated fraction of such tissue, organ or leukocytes or a cell type sample. Preferably, said mammal is a mouse, goat, dog, pig, cat, cow rat, monkey or human. The samples can be suitably pooled, if required.

Another preferred aspect of the method according to the present invention then further comprises the step of concluding on the immune status of said mammal based on said basophil granulocytes. The basophil granulocytes can be quantified and be used as a benchmark to relatively quantify further detailed subpopulations, or it can be used as a predictive and/or screening and/or diagnostic and/or prognostic and/or adverse events detecting factor, or it can be used to finally detect this population to determine the overall immune activity status.

In yet another preferred embodiment of the methods according to the present invention, the mammal suffers from or is likely to suffer from autoimmune diseases, transplant rejections, infection diseases, cancer, and/or allergy as but not limited to Trypanosoma cruzi-infection, Malaria and HIV infection; Hematologic Malignancies as but not limited to chronic Myelogenous Leukemia, Multiple Myeloma, Non-Hodgkin's Lymphoma, Hodgkin's Disease, chronic Lymphocytic Leukemia, Graft versus Host and Host versus Graft Disease, Mycosis fungoides, Extranodal T cell lymphoma, Cutaneous T cell lymphomas, Anaplastic large cell lymphoma, Angioimmunoblastic T cell lymphoma and other T-cell, B-cell and NK cell neoplasms, T cell deficiencies such as but not limited to lymphocytopenia, severe combined immunodeficiency (SCID), Omenn syndrome, Cartilage-hair hypoplasia, acquired immune deficiency syndrome (AIDS), and hereditary conditions such as DiGeorge syndrome (DGS), chromosomal breakage syndromes (CBSs), multiple sclerosis, rheumatoid arthritis, systemic lupus erythematosus, Sjögren's syndrome, systemic sclerosis, dermatomyositis, primary biliary cirrhosis, primary sclerosing cholangitis, ulcerative colitis, Crohn's disease, psoriasis, vitiligo, bullous pemphigoid, alopecia areata, idiopathic dilated cardiomyopathy, type 1 diabetes mellitus, Graves' disease, Hashimoto's thyroiditis, myasthenia gravis, IgA nephropathy, membranous nephropathy, and pernicious anemia; and B-cell and T-cell combined disorders such as but not limited to ataxia telangiectasia (AT) and Wiskott-Aldrich syndrome (WAS); and carcinomas such as but not limited to breast cancer, colorectal cancer, gastric cancer, pancreatic cancer, hepatocellular carcinoma, cholangiocarcinoma, melanoma, and head and neck cancer.

Another preferred aspect of the method according to the present invention then relates to a method as above, further comprising measuring and/or monitoring the amount of basophil granulocytes in response to chemical and/or biological substances that are provided to said mammal, i.e. in response to a treatment of said patient. Said method comprises the steps as above, and comparing said relative amount of said cells as identified to a sample taken earlier or in parallel from the same mammal, and/or to a control sample. Based on the results as provided by the method(s) of the invention, the attending physician will be able to conclude on the immune status of the patient, and adjust a treatment of the underlying disease accordingly.

Preferably, said method is performed without a step of purifying and/or enriching cells, preferably in whole blood and/or non-trypsinized tissue, or any other biological sample potentially containing said basophil granulocytes as e.g. a sample for cell transfer into a patient.

Another preferred aspect of the method according to the present invention then relates to a method as above, further comprising formulating said basophil granulocytes as identified for transplantation into a patient. Pharmaceutical preparations for these purposes and methods for their production are performed according to methods known in the art of transplantation medicine.

Another preferred aspect of the method according to the present invention relates to an oligomer according to any of SEQ ID NO: 4 to 11, or an amplicon according to SEQ ID NO: 1 to 3.

Yet another preferred aspect of the present invention then relates to a kit for identifying, quantifying, and/or monitoring basophil granulocytes in a mammal based on the analysis of the bisulfite accessibility of CpG positions in the gene region of MCC, comprising components for performing a method according to invention as described herein, in particular a kit comprising a) a bisulfite reagent, and b) materials for the analysis of the methylation status of CpG positions selected from the CpG positions in the region according to SEQ ID NO: 1, such as an oligomer selected from the sequences according to SEQ ID NO: 4 to 11.

The present invention also encompasses the use of oligomers or amplicon or a kit according to the present invention for identifying and/or for monitoring basophil granulocytes in a mammal as described herein.

As mentioned above, recently three new cytosine modifications were discovered. Therefore, it is expected that future scientific findings will correct epigenetic patterns of modification described in the past. These past patterns of cytosine modification encompass bisulfite convertible (non-methylated, non-modified) and non-convertible (methylated, modified) cytosine. Both termini need to be corrected, as described. According to the novel scientific findings (i) non-bisulfite convertible cytosine encompasses 5-methylcytosine (mC) and 5-hydroxymethylcytosine (hmC), and (ii) bisulfite convertible (i.e. the "bisulfite convertibility") cytosine encompasses 5-formylcytosine (fC), 5-carboxycytosine (cC), as well as non-modified cytosine.

Additionally, earlier inventions are based on (i) the ratio of bisulfite convertible cytosine to whole amount of chromatin (cell-type independent, 100% bisulfite convertible DNA locus) or (ii) on the ratio of bisulfite convertible cytosine (fC, cC, non-modified cytosine) to non-bisulfite convertible cytosine (hmC and mC). These ratios characterize cell type, cell differentiation, cell stage as well as pathological cell stages. Therefore, new techniques will result in novel, more specific ratios and might supplement current cell specific, cell state specific as well as pathological patterns of epigenetic modifications and, therefore, define potential novel biomarkers. Novel ratios to be discovered as biomarkers can be defined as:

Biomarker Ratio=$a/b$ $a=\Sigma(C$ and/or $mC$ and/or $hmC$ and/or $fC$ and/or $cC)$ $b=\Sigma(C$ and/or $mC$ and/or $hmC$ and/or $fC$ and/or $cC)$, whereby a and b differs from each other by one to four kinds of modifications. Discovery of novel DNA modifications will enlarge this enumeration.

For the purpose of definition for the present application, "epigenetic modifications" in the DNA sequence is referred to by the terminology of (i) bisulfite convertible cytosine (5-formylcytosine, (fC) and/or 5-carboxycytosine (cC)) and (ii) non-bisulfite convertible cytosine ((including 5-methylcytosine (mC), 5-hydroxymethylcytosine, (hmC)). As both kinds of methylation, mC and hmC, are not bisulfite convertible, it is not possible to distinguish between these two. Likewise, fC, cC as well as non-modified cytosine are bisulfite convertible and can also not be distinguished from each other as well. The term "methylated" DNA encompasses mC as well as hmC. The term "non-methylated" DNA encompasses fC, cC, and non-modified DNA. It is expected that novel variants of DNA modifications will be discovered in future. Each type of modification will be either bisulfite convertible or not. However, since the present method reliably distinguishes between the two groups, these novel modifications will also be usable as markers.

Furthermore, apart from the modifications of DNA, also histones undergo posttranslational modifications that alter their interaction with DNA and nuclear proteins. Modifications include methylation, acetylation, phosphorylation, ubiquitination, sumoylation, citrullination, and ADP-ribosylation. The core of the histones H2A, H2B, and H3 can also be modified. Histone modifications act in diverse biological processes such as gene regulation, DNA repair, chromosome condensation (mitosis) and spermatogenesis (meiosis). Also for these modifications a specific pattern of modification is specific for different cell types, cell stages, differentiation status and such a pattern can be analyzed for bisulfite convertibility or similar methods in order to identify certain cells and cell stages. The present invention also encompasses a use of these modifications.

In summary, using the MCC genetic region and in particular the amplicon as described herein as a marker, the inventors very specifically identified, quantified and particularly differentiated basophil granulocytes, and in their relation to other cell types in a sample, for example to other blood cells.

The invention will now be further described based on the following examples and with reference to the accompanying figures and the sequence listing, without being limited thereto. For the purposes of the present invention, all references as cited herein are incorporated by reference in their entireties.

FIG. 1 shows the analysis of CpG sites on amplicon No. 2694 (SEQ ID NO: 1) according to the invention. The horizontal boxes in the table correspond to the CpG positions in the amplicon as analyzed (e.g. CpG 1 to 4, and CpG 6 to 10) with the positions indicated (e.g. AMP2694:57, corresponding to CpG 1 at position 57 of AMP2694, . . . etc.), and the columns correspond to the cell types as analyzed.

SEQ ID NO: 1 shows the genomic sequence of amplicon AMP2694 according to the present invention.

SEQ ID NOs: 2 and 3 show the sequences of bisulfite-converted target-regions of the preferred qPCR-assay-systems of the invention.

SEQ ID NOs: 4 to 11 show the sequences of specific oligomers (primers and probes) according to the present invention.

EXAMPLES

Example 1

In order to identify basophil granulocytes, qPCR was performed on bisulphite converted samples stemming from the human genomic region according to the following sequence (AMP2694, SEQ ID NO: 1), relevant CpGs are indicated in bold:

TGCTCTGGTCCTCCTTGCCCAAGAGGTGTGGGGATGGGTGTGGTGGAGGC

ACAGTCCGGGGTTGGTCTCGCCTGCCGCACGCCTGTTCAGTAGCCTTTTA

ATGAACTCAGTGACTCAGCGCTGTCCCTCCCCCACCGGCCTCGGATCTCA

TTCCTCTCAATCGCACTGATGCCCATGTGACAGCACGTTGTCTCCACCGA

GACTAATCCCTTATCAATAAGAGCTTTCAGCACGGCCCAGACCAGATTAC

TCTGTCTCACAACCACTTTGCTGACCTGCCCGGGGGGCCACCGAATACTC

CCCGAGCGCATACTATTTACAGAAGAGTCAAGATAAGCCGGATCACTTGG

CGTGATTATTTCGCTTCCAAAGTTTGTGGCTTTAACAAAGCAAACCCACA

TTCAAC

The bisulfite-converted target-regions of the preferred qPCR-assay-system as developed were:

TpG-specific (SEQ ID NO: 2, relevant positions bold and underlined):

TACTCTAATCCTCCTTACCCAAAAAATATAAAAATAAATATAATAAAAAC

ACAATC<u>CA</u>AAATTAATCT<u>CA</u>CCTAC<u>CA</u>CAC<u>A</u>CCTATTCAATAACCTTTTA

ATAAACTCAATAACTCAA<u>CA</u>CTATCCCTCCCCCAC<u>CA</u>ACCT<u>CA</u>AATCTCA

TTCCTCTCAAT<u>CA</u>CACTAATACCCATATAACAACA<u>CA</u>TTATCTCCAC<u>CAA</u>

AACTAATCCCTTATCAATAAAAACTTTCAACA<u>CA</u>ACCCAAACCAAATTAC

TCTATCTCACAACCACTTTACTAACCTACC<u>CA</u>AAAAACCAC<u>CA</u>ATACTC

CCC<u>AA</u>AC<u>CA</u>CATACTATTTACAAAAAAATCAAAATAAAC<u>CA</u>AATCACTTAA

<u>CA</u>TAATTATTT<u>CA</u>ACTTCCAAAATTTATAACTTTAACAAAACAAACCCAC
ATTCAAC

CpG-specific: (SEQ ID NO: 3, relevant positions bold and underlined):

TACTCTAATCCTCCTTACCCAAAAAATATAAAAATAAATATAATAAAAAC

ACAATC<u>CG</u>AAATTAATCT<u>CG</u>CCTAC<u>CG</u>CAC<u>G</u>CCTATTCAATAACCTTTTA

ATAAACTCAATAACTCAA<u>CG</u>CTATCCCTCCCCCAC<u>CG</u>ACCT<u>CG</u>AATCTCA

TTCCTCTCAAT<u>CG</u>CACTAATACCCATATAACAACA<u>CG</u>TTATCTCCAC<u>CGA</u>

AACTAATCCCTTATCAATAAAAACTTTCAACA<u>CG</u>ACCCAAACCAAATTAC

TCTATCTCACAACCACTTTACTAACCTACC<u>CG</u>AAAAACCAC<u>CG</u>AATACTC

CCC<u>CG</u>AA<u>CG</u>CATACTATTTACAAAAAAATCAAAATAAAC<u>CG</u>AATCACTTAA

<u>CG</u>TAATTATTT<u>CG</u>CTTCCAAAATTTATAACTTTAACAAAACAAACCCACA
TTCAAC

The following primers and probe were used for the amplification:

```
Forward applification 2694r      TACTCTAATCCTCCTTACCCCAA
primer                           (SEQ ID No. 4)

Reverse amplification 2694q      GTTGAATGTGGGTTTGTTTT
primer                           (SEQ ID No. 5)

Forward primer        2694r_T_fw AACACAATCCAAAATTAATCTCA
TpG-specific                     (SEQ ID No. 6)

Reverse primer        2694q_T_rev GAGGAATGAGATTTGAGGTTG
TpG-specific                     (SEQ ID No. 7)

Probe TpG-specific    2694_TP    ATTGAATAGGCGTGCGGTAGGCGA
                                 (SEQ ID No. 11)

Forward primer        2694r_C_fw AACACAATCCGAAATTAATCTCGC
CpG-specific                     (SEQ ID No. 9)

Reverse primer        2694q_C_rev GGAATGAGATTCGAGGTCG
CpG-specific                     (SEQ ID No. 10)

Probe CpG-specific    2964_CP    AGGTTATTGAATAGGTGTGTGGTAGGTGAG
                                 (SEQ ID No. 8)
```

Even though not explicitly disclosed in this example, equally preferred are the other bisulfite strands and their according primers.

The specificity of the TpG-specific PCR-system was demonstrated using test-templates (plasmid-DNA) as shown in the following table. The table shows the measurement of purified cell types using the TpG specific assay for MCC—and thus basophil granulocytes—compared to two alternative "control systems". The cell types in the table are abbreviated as follows: MOC29—purified CD14 Monocytes; CTL11—cytotoxic T cells; Grc32—all CD15 granulocytes; NKC—CD56 Natural killer cells; THC13 T helper cells; eGRC—eosinophil basophils; BLC28-B cells; nGRC03—Neutrophils; NKT—Natural killer T cells and bGRC—basophil granulocytes. In the upper panel the control amplification system is actually the CpG specific system. At this point this system is the better control system as it should be comparably low in cells with a high number of cells genomically unmodified (demethylated) at the analyzed position and high numbers of cells with a methyl-modified position. The final analysis system however relies on a system where all cells are equally measured, and only the specific cells show amplification at the given epigenetically modified locus.

|  | CP Value | Plasmid Units | C.V. (%) | CP Value | Plasmid Units | C.V. (%) | bGRC [%] | S.D. | C.V. (%) |
|---|---|---|---|---|---|---|---|---|---|
|  | TpG specific PCR-System | | | CpG specific PCR-System | | | | | |
| MOC29 | 36.45 | 5.00 | 27.42 | 26.37 | 7036.67 | 3.54 | 0.07 | 0.02 | 23.81 |
| CTL11 | 37.12 | 3.59 | 60.18 | 27.46 | 3193.33 | 1.54 | 0.11 | 0.06 | 52.15 |
| GRC32 | 35.53 | 9.74 | 34.36 | 26.11 | 8510.00 | 2.45 | 0.11 | 0.04 | 29.80 |
| NKC25 | 35.36 | 11.28 | 39.28 | 26.29 | 7493.33 | 1.36 | 0.15 | 0.05 | 34.02 |
| THC13 | 36.95 | 3.50 | 24.10 | 26.34 | 7233.33 | 1.05 | 0.05 | 0.01 | 20.96 |
| eGRC01 | 33.43 | 41.50 | 13.83 | 25.98 | 9353.33 | 1.10 | 0.44 | 0.05 | 12.08 |
| BLC28 | 35.42 | 10.31 | 25.64 | 26.28 | 7546.67 | 0.54 | 0.14 | 0.03 | 22.23 |
| nGRC03 | 38.47 | 2.00 | 91.45 | 25.91 | 9826.67 | 0.62 | 0.02 | 0.02 | 79.30 |
| NKT20 | 37.68 | 2.13 | 33.36 | 28.72 | 1286.67 | 1.62 | 0.17 | 0.05 | 28.97 |
| bGRC06 | 26.50 | 5523.33 | 1.21 | 28.53 | 1476.67 | 3.20 | 78.90 | 1.34 | 1.39 |
|  | TpG specific PCR-System | | | GAPDH specific PCR-System | | | | | |
| MOC29 | 36.45 | 5.00 | 27.42 | 25.59 | 6936.67 | 1.83 | 0.07 | 0.02 | 23.81 |
| CTL11 | 37.12 | 3.59 | 60.18 | 26.69 | 3063.33 | 1.99 | 0.12 | 0.06 | 52.15 |
| GRC32 | 35.53 | 9.74 | 34.36 | 25.54 | 7220.00 | 1.77 | 0.13 | 0.04 | 29.80 |
| NKC25 | 35.36 | 11.28 | 39.28 | 25.57 | 7060.00 | 0.25 | 0.16 | 0.05 | 34.02 |
| THC13 | 36.95 | 3.50 | 24.10 | 25.53 | 7230.00 | 2.28 | 0.05 | 0.01 | 20.96 |
| eGRC01 | 33.43 | 41.50 | 13.83 | 25.10 | 10046.67 | 1.85 | 0.41 | 0.05 | 12.08 |
| BLC28 | 35.42 | 10.31 | 25.64 | 25.44 | 7730.00 | 1.23 | 0.13 | 0.03 | 22.23 |
| nGRC03 | 38.47 | 2.00 | 91.45 | 25.19 | 9356.67 | 3.64 | 0.02 | 0.02 | 79.30 |
| NKT20 | 37.68 | 2.13 | 33.36 | 27.90 | 1286.67 | 2.37 | 0.17 | 0.05 | 28.97 |
| bGRC06 | 26.50 | 5523.33 | 1.21 | 25.84 | 5743.33 | 1.06 | 96.17 | 1.34 | 1.39 |

The invention claimed is:

1. A method for producing an amplicon from a region of mutated in colorectal cancer (MCC) gene, the method comprising
   a) bisulfite treating isolated genomic DNA from a mammalian cell sample to generate bisulfite treated DNA, and
   b) producing the amplicon by amplifying from the bisulfite treated DNA the region of the MCC gene comprising nucleotides 57 to 234 of SEQ ID NO: 1 prior to bisulfite treatment, wherein the amplifying is performed with a polymerase chain reaction (PCR) using methylation-specific primers, and
   wherein the amplicon comprises CA at CA positions 186, 198, and 233 relative to SEQ ID NO: 2.

2. The method according to claim 1, wherein the amplicon further comprises CA at one or more CA positions selected from positions 57, 69, 76, 80, 119, 136, 142, 162, 339, 351, and 362 relative to SEQ ID NO: 2.

3. The method according to claim 1, further comprising detecting the CA by a method selected from a methylation specific enzymatic digest, bisulfite sequencing, promoter methylation analysis, CpG island methylation analysis, MSP, HeavyMethyl, MethyLight, and Ms-SnuPE.

4. The method according to claim 1, wherein said cell sample is obtained from a body fluid, a tissue, or an organ.

5. The method according to claim 1, wherein said method is performed without a step of purifying and/or enriching said cell sample.

6. The method according to claim 1, wherein said cell sample is from a mammal that suffers from or is likely to suffer from autoimmune diseases, transplant rejections, infection diseases, cancer, and/or allergy.

7. The method of claim 1, wherein the method is performed using a kit comprising:
   a) a bisulfite reagent, and
   b) materials for detecting the CA.

8. The method of claim 1, wherein the amplifying uses an oligomer comprising the sequence of any one of SEQ ID NOs: 4-7 or 11, or wherein the method produces the amplicon comprising SEQ ID NO: 2.

9. The method according to claim 1, wherein the amplicon further comprises CA at two or more CA positions selected from CA positions 57, 69, 76, 80, 119, 136, 142, 162, 339, 351, and 362 of SEQ ID NO: 2.

10. The method according to claim 1, wherein the mammalian cell sample is whole blood and/or non-trypsinized tissue.

11. The method of claim 1, wherein the amplicon further comprises CA at three or more CA positions selected from CA positions 57, 69, 76, 80, 119, 136, 142, and 162 of SEQ ID NO: 2.

12. The method of claim 1, wherein the amplicon further comprises CA at CA positions 339, 351, and 362 of SEQ ID NO: 2.

13. The method of claim 1, wherein the amplifying uses an oligomer of SEQ ID NO: 11.

14. The method of claim 1, wherein the amplicon comprises SEQ ID NO: 2.

15. The method of claim 1, wherein the region of the MCC gene comprises nucleotides 1 to 234 of SEQ ID NO: 1 prior to bisulfite treatment.

* * * * *

SEQUENCE LISTING

<160> NUMBER OF SEQ ID NOS: 11

<210> SEQ ID NO 1
<211> LENGTH: 406
<212> TYPE: DNA
<213> ORGANISM: Homo sapiens

<400> SEQUENCE: 1

```
tgctctggtc ctccttgccc aagaggtgtg gggatgggtg tggtggaggc acagtccggg    60
gttggtctcg cctgccgcac gcctgttcag tagccttta atgaactcag tgactcagcg   120
ctgtccctcc cccaccggcc tcggatctca ttcctctcaa tcgcactgat gcccatgtga   180
cagcacgttg tctccaccga gactaatccc ttatcaataa gagctttcag cacggcccag   240
accagattac tctgtctcac aaccactttg ctgacctgcc cggggggcca ccgaatactc   300
cccgagcgca tactatttac agaagagtca agataagccg gatcacttgg cgtgattatt   360
tcgcttccaa agtttgtggc tttaacaaag caaacccaca ttcaac                  406
```

<210> SEQ ID NO 2
<211> LENGTH: 406
<212> TYPE: DNA
<213> ORGANISM: Homo sapiens

<400> SEQUENCE: 2

```
tactctaatc ctccttaccc aaaaaatata aaataaaata taataaaaac acaatccaaa    60
attaatctca cctaccacac acctattcaa taaccttta ataaactcaa taactcaaca   120
ctatccctcc cccaccaacc tcaaatctca ttcctctcaa tcacactaat acccatataa   180
caacacatta tctccaccaa aactaatccc ttatcaataa aaactttcaa cacaacccaa   240
accaaattac tctatctcac aaccacttta ctaacctacc caaaaaacca ccaaatactc   300
cccaaacaca tactatttac aaaaaaatca aaataaacca aatcacttaa cataattatt   360
tcacttccaa aatttataac tttaacaaaa caaacccaca ttcaac                  406
```

<210> SEQ ID NO 3

-continued

```
<211> LENGTH: 406
<212> TYPE: DNA
<213> ORGANISM: Homo sapiens

<400> SEQUENCE: 3
tactctaatc ctccttaccc aaaaaatata aaaataaata taataaaaac acaatccgaa      60
attaatctcg cctaccgcac gcctattcaa taacctttta ataaactcaa taactcaacg     120
ctatccctcc cccaccgacc tcgaatctca ttcctctcaa tcgcactaat acccatataa     180
caacacgtta tctccaccga aactaatccc ttatcaataa aaactttcaa cacgacccaa     240
accaaattac tctatctcac aaccacttta ctaacctacc cgaaaaacca ccgaatactc     300
cccgaacgca tactatttac aaaaaaatca aaataaaccg aatcacttaa cgtaattatt     360
tcgcttccaa aatttataac tttaacaaaa caaacccaca ttcaac                   406

<210> SEQ ID NO 4
<211> LENGTH: 22
<212> TYPE: DNA
<213> ORGANISM: Homo sapiens

<400> SEQUENCE: 4
tactctaatc ctccttaccc aa                                              22

<210> SEQ ID NO 5
<211> LENGTH: 20
<212> TYPE: DNA
<213> ORGANISM: Homo sapiens

<400> SEQUENCE: 5
gttgaatgtg ggtttgtttt                                                 20

<210> SEQ ID NO 6
<211> LENGTH: 23
<212> TYPE: DNA
<213> ORGANISM: Homo sapiens

<400> SEQUENCE: 6
aacacaatcc aaaattaatc tca                                             23

<210> SEQ ID NO 7
<211> LENGTH: 21
<212> TYPE: DNA
<213> ORGANISM: Homo sapiens

<400> SEQUENCE: 7
gaggaatgag atttgaggtt g                                               21

<210> SEQ ID NO 8
<211> LENGTH: 24
<212> TYPE: DNA
<213> ORGANISM: Homo sapiens

<400> SEQUENCE: 8
attgaatagg cgtgcggtag gcga                                            24

<210> SEQ ID NO 9
<211> LENGTH: 24
<212> TYPE: DNA
<213> ORGANISM: Homo sapiens

<400> SEQUENCE: 9
aacacaatcc gaaattaatc tcgc                                            24
```

```
<210> SEQ ID NO 10
<211> LENGTH: 19
<212> TYPE: DNA
<213> ORGANISM: Homo sapiens

<400> SEQUENCE: 10
ggaatgagat tcgaggtcg                                               19

<210> SEQ ID NO 11
<211> LENGTH: 30
<212> TYPE: DNA
<213> ORGANISM: Homo sapiens

<400> SEQUENCE: 11
aggttattga ataggtgtgt ggtaggtgag                                   30
```